(12) United States Patent
Hines et al.

(10) Patent No.: US 10,593,131 B2
(45) Date of Patent: Mar. 17, 2020

(54) SYSTEMS AND METHODS FOR REDUCING OCCUPATIONAL DERMATITIS

(71) Applicant: DEB IP LIMITED, Denby Derbyshire (GB)

(72) Inventors: John Hines, Denby (GB); Dean Limbert, Denby (GB)

(73) Assignee: DEB IP LIMITED (GB)

( * ) Notice: Subject to any disclaimer, the term of this patent is extended or adjusted under 35 U.S.C. 154(b) by 0 days.

(21) Appl. No.: 15/540,685

(22) PCT Filed: Sep. 23, 2016

(86) PCT No.: PCT/IB2016/001362
§ 371 (c)(1),
(2) Date: Jun. 29, 2017

(87) PCT Pub. No.: WO2017/051244
PCT Pub. Date: Mar. 30, 2017

(65) Prior Publication Data
US 2017/0358149 A1 Dec. 14, 2017

(30) Foreign Application Priority Data
Sep. 25, 2015 (GB) .................................. 1517000.4

(51) Int. Cl.
*G08B 23/00* (2006.01)
*G07C 1/02* (2006.01)
(Continued)

(52) U.S. Cl.
CPC .................. *G07C 1/02* (2013.01); *A47K 5/06* (2013.01); *A47K 5/12* (2013.01); *A61L 2/16* (2013.01);
(Continued)

(58) Field of Classification Search
None
See application file for complete search history.

(56) References Cited

U.S. PATENT DOCUMENTS

| 5,945,910 | A | 8/1999 | Gorra |
|---|---|---|---|
| 7,271,728 | B2 | 9/2007 | Taylor et al. |
| 8,395,515 | B2 | 3/2013 | Tokhtuev et al. |
| 2002/0150198 | A1 | 10/2002 | Thompson et al. |
| 2006/0273915 | A1* | 12/2006 | Snodgrass ............ G08B 21/245 340/573.1 |

(Continued)

FOREIGN PATENT DOCUMENTS

WO  2015061718 A1  4/2015

OTHER PUBLICATIONS

PCT International Search Report and Written Opinion for Application No. PCT/IB2016/001362 dated Feb. 21, 2017, 9 pages.
(Continued)

*Primary Examiner* — Adolf Dsouza
(74) *Attorney, Agent, or Firm* — McAndrews, Held & Malloy, Ltd.

(57) ABSTRACT

A system for reducing occupational dermatitis at a work place the system comprising at a facility: one or more dispensers configured to dispense a pre-work hand product; one or more dispensers configured to dispense a washing and cleansing product; one or more dispensers configured to dispense a conditioning product; one or more dispensers configured to dispense a post-work product; a dispenser usage monitoring system; each of said plurality of dispensers in communication with the dispenser usage compliance system and configured to provide a signal to the dispenser usage monitoring system, indicative of usage of the dispenser, wherein the dispenser usage monitoring system is configured to determine usage of the plurality of the dispensers against a skin care regime.

4 Claims, 2 Drawing Sheets

(51) Int. Cl.
*A47K 5/12* (2006.01)
*G06Q 50/22* (2018.01)
*A61L 2/16* (2006.01)
*A61L 2/18* (2006.01)
*G07C 11/00* (2006.01)
*G07C 3/00* (2006.01)
*G06Q 10/06* (2012.01)
*A47K 5/06* (2006.01)
*G07F 17/18* (2006.01)

(52) U.S. Cl.
CPC ............... *A61L 2/18* (2013.01); *G06Q 10/06* (2013.01); *G06Q 50/22* (2013.01); *G07C 3/00* (2013.01); *G07C 11/00* (2013.01); *G07F 17/18* (2013.01)

(56) References Cited

U.S. PATENT DOCUMENTS

| | | |
|---|---|---|
| 2010/0173581 A1 | 7/2010 | Dolan |
| 2011/0316701 A1* | 12/2011 | Alper ................... G08B 21/245 |
| | | 340/573.1 |
| 2015/0134354 A1 | 5/2015 | Alper et al. |
| 2016/0093195 A1 | 3/2016 | Ophardt |

OTHER PUBLICATIONS

"Skin Care & Hygiene," A Fresh Approach to Hygiene 2 (2011): Kingfisher Sales and Marketing, Web <http:/kingfishersales.com/KingfisherCatalogueWeb.pdf>, May 6, 2011, pp. 3-28.

* cited by examiner

SYSTEMS AND METHODS FOR REDUCING OCCUPATIONAL DERMATITIS

CROSS-REFERENCE TO RELATED APPLICATIONS/INCORPORATION BY REFERENCE

The present application is the U.S. national phase under § 371 of International Application No. PCT/IB2016/001362, having an international filing date of Sep. 23, 2016, which claims priority to EP Patent Application No. 15170004, filed Sep. 25, 2015. Each of the above-mentioned prior-filed applications is hereby expressly incorporated herein by reference in its entirety.

FIELD OF INVENTION

The present invention relates to system and method for reducing occupational dermatitis amongst workers.

BACKGROUND TO THE INVENTION

In the workplace it is known to provide hand washing facilities. In some environments hand washing may be of particular importance. For example in medical environments effective hand washing is of particular importance in order to help prevent the spread of disease or infection. In further environments, such as in factories, hand washing is required after contact with certain materials.

Whilst the population has become more aware, through training, of the importance of hand washing the provision of effective hand washing materials, such as automatic dispensers, has increased. However, it has also been found that in professions where persons are repeatedly washing their hands the repeated, long term, exposure to hand washing agents has led to an increase in occupational dermatitis in amongst such workers. Skin disease is arguably the most common occupational disease, with occupational contact dermatitis (CD) accounting for up to 95% of all occupational skin disease; irritant contact dermatitis accounts for the majority of these cases. Contact dermatitis can have serious adverse impact on social and occupational aspects of life, including lost days at work, and threat to employment.

Irritation may result from unprotected and repeated exposure to irritants such as detergents, soaps, solvents, water, food ingredients, and cutting oils or fluids. Over time, these irritants continuously harm the skin and may eventually predispose to allergic CD, which becomes a chronic condition. However, removing irritants is an impractical and improbable solution in many workplaces afflicted by CD including agricultural workers, beauticians, chemical workers, cleaners, construction workers, cooks, electronics workers, hairdressers, health and social care workers, machine operators, mechanics, metalworkers, and vehicle assemblers. Accordingly, even when a person experiences occupational dermatitis it is important that the person continues with their hand washing, or exposing their hands to the source of irritation, in order to prevent the spread of infection, disease, or simply to be able to perform their job.

In order to overcome some of the above problems there is provided a system and method for reducing occupational dermatitis whilst ensuring that the person maintain good hygiene and hand washing practices.

There is provided a system for reducing occupational dermatitis at a work place the system comprising at a facility: one or more dispensers configured to dispense a pre-work hand product; one or more dispensers configured to dispense a washing or cleansing product; one or more dispensers configured to dispense a conditioning product; one or more dispensers configured to dispense a post-work product; a dispenser usage monitoring system; each of said plurality of dispensers in communication with the dispenser usage compliance system and configured to provide a signal to the dispenser usage monitoring system, indicative of usage of the dispenser, wherein the dispenser usage monitoring system is configured to determine usage of the plurality of the dispensers against a skin care regime.

The use of the pre-work product provides an effective barrier to the hand washing product which the person will use during the course of their work. The use of the post-work product provides a product to repair any potential damage to the skin caused by the exposure to the hand washing product during the course of the user's work. Advantageously the method allows for the user to continue with their effective hand washing procedures and to use products which are known to be effective. This identifies a best practice routine for workers to adopt in the workplace where they might be exposed to skin irritants.

A further aspect of the invention is the use of monitoring systems for individual users, and groups of users, to ensure compliance of the user with the above identified best practice three wash protocol. Where users, or groups of users, are identified as not complying with the three step skincare protocol appropriate remedial action may be undertaken to help ensure compliance with the best practice protocol across a facility or within a group of one or more users.

BRIEF DESCRIPTION OF THE DRAWINGS

An embodiment of the invention is now described, by way of example only, with reference to the accompanying drawing in which.

DETAILED DESCRIPTION OF AN EMBODIMENT

According to an aspect of the invention, there is provided a new system and methodology for reducing occupational dermatitis.

In particular the present invention provides a methodology which can be introduced into a workplace and successfully monitored. The present invention addresses the problem in a holistic manner based on four perspectives: clinical evidence, integration into workflow, trainability for high user acceptance, and generally applicability to different workplace environments (Table 1).

TABLE 1

Four perspectives to consider for holistic prevention program.

Figure 1:
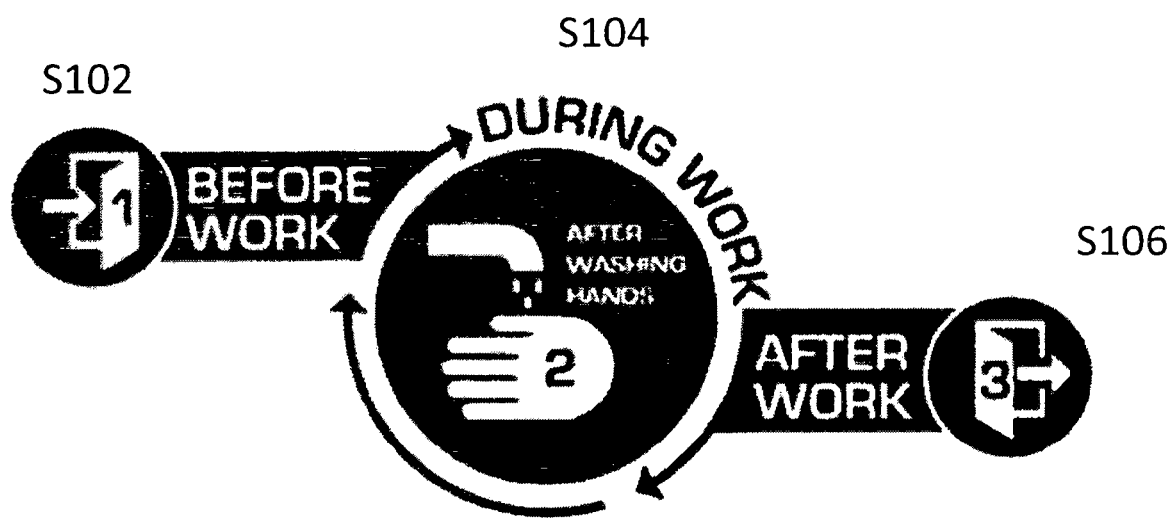
FIG. 1 is a flowchart of the hand washing methodology according to an aspect of the invention.

Consistent with clinical evidence for prevention of irritant contact dermatitis in the workplace
Integrates seamlessly into work environment and daily workflow
Ease of learning results in high user acceptance
General enough to be applied to the various occupational settings that are at high risk of exposure to irritants An important aspect of the invention is the realisation that whilst reducing, or indeed removal of, the exposure to irritants would prevent the many cases of CD in many environments the removal of the irritants is impractical, or indeed impossible. These irritants are inherent to everyday work such as oils in mechanic shops, metal working fluids, shampoos in hairdresser salons, and chemicals in cleaner facilities. Even hand washing with water and detergents in so-called wet-work may be harmful, There is provided a three stage methodology as shown in FIG. 1.

The process therefore defines a best practice protocol to be observed so as to reduce the risk of, or alleviate, occupational dermatitis across a group of users. The methodology may be implemented in any industrial, or clinical, environment where there is a risk of CD.

At step S102 the user applies a pre-work product.

An aspect of the invention is the application of a pre-work product to the user's hands before their exposure to the irritants. Pre-work products are often known as barrier products however as part of the training and education aspect of the invention it is preferred to utilise the terminology pre-work product. The term barrier product is less preferred as it may infer a sense of false protection to workers, who subsequently do not practice appropriate safety measures in the workplace, making them more complacent to more effective preventive measures. Accordingly, the term pre-work product is preferred.

In all hand product application scenarios, it is assumed that workers are educated that hands must be freshly washed, or previously cleansed, in order to make certain the skin is free of irritants so as not to trap them under product applications. Furthermore, products must be applied thoroughly with special attention to inter-digital areas and nail beds. The 3-moments method reflects measurable events in the workplace (i.e. before entering work at the beginning of a shift, after washing hands during work, and exiting work after a work shift), and should not be confused with different moisturizer types.

Therefore at step S102 before starting a shift with occupational exposure to irritants, workers must apply a pre-work product as a supporting layer in the skin's defence mechanism. The pre-work product also facilitates removal of irritants from the skin surface by capturing them and washing them off at the next hand-washing event (as per step S104 defined below).

In an embodiment of the invention to ensure pre-work product application in a workplace, pre-work product dispensers are installed at all work stations with visible and clear instructions to workers to apply the recommended portion (e.g. specified by the number of pumps required from the dispenser) as they enter and before any contact with work tools or materials.

The specific composition of the pre-work product depends on the irritant to which the worker is exposed during their shift, as some products are more effective than others for acting as a pre-work product for a given irritant. Examples of preferred pre-work products are Travabon Special PURE® for exposure to water-insoluble workplace substances such as solvents, metal-working oils and resins, Stokoderm Protect PURE® for exposure to water and non-water based contaminants including dry powders and Stokoderm Grip PURE® for exposure to both oil-based and water-based materials.

Once the worker has applied their pre-work product the work begins their shift in the normal manner.

At step S104 the worker continues to wash their hands when required during the course of the day.

After each exposure to work tools and materials, the worker washes or cleanses their hands, or as and when required. An aspect of the invention is once the hands have been cleaned of any irritant, is that the worker either reapplies the pre-work product and returns to work or applies conditioning products to the skin exposed to detergents and other abrasive or skin-drying substances that may compromise its integrity and deplete the skin's natural moisturizing factors and oils. The choice of whether to reapply a pre work product or a conditioning product is based upon the intervening time between the hand wash event and returning to work. It is important to note that hand product application preferably takes place after hand washing and drying, and prior to sanitizing with any alcohol-based substances.

In an embodiment of the invention both pre work product and conditioning product dispensers are mounted near all hand-wash areas throughout the work facility with visible and clear instructions to workers to apply the recommended portion after each hand washing. Accordingly, once the worker has washed their hands in the normal manner the worker applies either a pre work product or a conditioning product as required.

At step S106 at the end of the user's shift the user applies a conditioning product, also known as a post-work product, to their hands.

Examples of the preferred post-work product include Stokolan Classic®, Stokolan Intense®, Stokolan Light PURE® and Stokolan Sensitive PURE®.

By applying a conditioning or post-work product the user is able to replenish any lost moisture and/or oils, allowing the skin to regenerate and repair any damage caused by exposure to the irritants during the course of the working shift.

A further aspect of the invention is the ability to monitor the uptake and acceptance of the new hand washing proposals, and if the levels of acceptance or use of a specific product are lower than a predetermined value to vary the amount dispensed. As the above invention defines a new methodology and accordingly requires a change in end user behaviour in order to successfully implement. The monitoring and reporting of user acceptance is therefore helpful in ensuring that the rates of occupational dermatitis are reduced.

Monitoring occurs via the established model of hand-hygiene compliance monitoring, in which there are three fundamental monitoring components: 1) establishing a denominator for the total number of hand product application events that are possible in a given period, 2) developing a sustainable method for measuring the number of events fulfilled in a given period (the numerator), and 3) calculating a baseline from which to gauge improvements over time. Preferably the monitoring in an embodiment occurs via an electronic monitoring system such as that described in PCT/GB2011/051206.

The compliance of a facility is preferably determined as (numerator)/(denominator)*100. Preferably the numerator is defined as the number of conditioning product application events, including both pre-work and post-work, as determined by the monitoring system. Preferably the denominator is defined as the total number of possible hand product application events which in an embodiment is determined as the number of hand washing events. In further embodiments the denominator may also include the number of employees entering the monitored area as an indicator of the number of pre-work product applications that should take place at the beginning of a working period.

Figure 2:
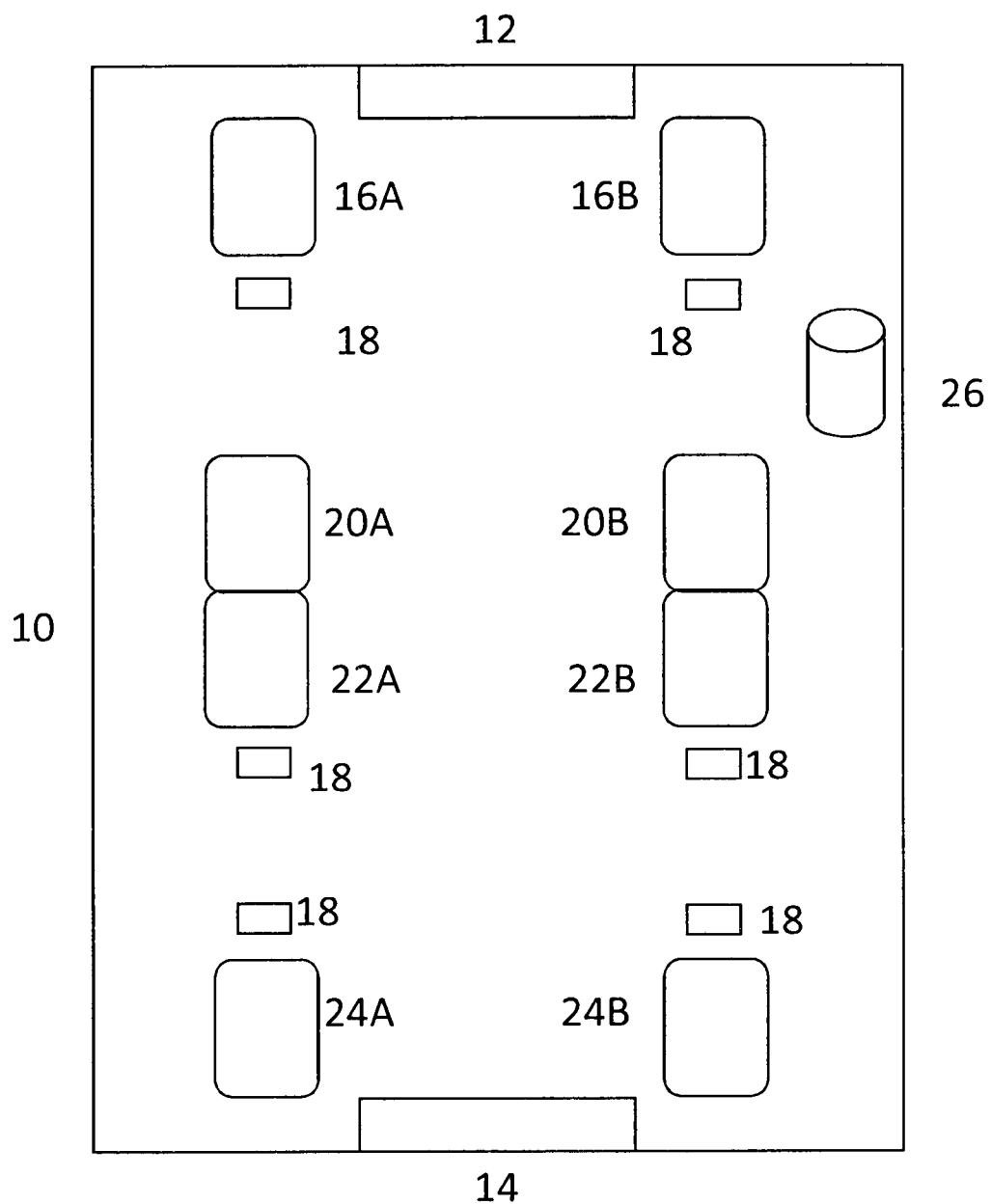
FIG. 2 is a schematic representation of the apparatus according to an aspect of the invention.

FIG. 2 a schematic representation of the apparatus according to an aspect of the invention.

There is shown a facility 10, having an entrance 12 and exit 14. At the entrance there are a plurality of pre-work product dispensers 16A, 16B configured to dispense pre-work product. Situated next to the pre-work product dispensers are educational posters 18 informing the users of the hand washing methodology to remind the users to apply the pre-work product before commencing work.

Within the facility 10 there are a plurality of dispensers configured to dispense hand sanitising lotion 20A, 20B and condition products 22A, 22B. Preferably the sanitising lotion and condition or post-work product dispensers are situated next to each other. Further educational posters 18 are placed near the dispensers.

By the exit of the facility there are plurality of conditioning or post-work product dispensers 24, 24A and further educational posters 18.

Located within the facility is a dispenser usage compliance system 26.

The layout provide in FIG. 2 is illustrative and will vary according to the layout of the facility 10.

The dispensers 16, 20, 22, 24 are, in a preferred embodiment, are dispensers which are in wireless communication with the dispenser usage compliance system 26. Upon each activation of a dispenser, a message is sent from the dispenser to the dispenser usage compliance system 26 to indicate a usage event. Such monitoring of usage is known in the art and enables compliance to be monitored.

An aspect of the invention is the ability to ensure compliance and to take remedial action when levels of compliance are determined to be low. Remedial action may take the form of: providing audio/visual alerts to the users; the use of posters detailing levels of compliance or reminding the users of the best practice protocol, in particular near the hand washing stations; providing onsite training to the users of the facility to reinforce the best practice protocol.

The invention claimed is:

1. A system for reducing occupational dermatitis at a work place, the system comprising:
   one or more dispensers at a facility configured to dispense a skin protection product;
   one or more dispensers at the facility configured to dispense a skin cleansing product;
   one or more dispensers at the facility configured to dispense a skin conditioning product;
   a dispenser usage monitoring system for monitoring use of said one or more dispensers configured to dispense skin protection product, said one or more dispensers configured to dispense skin cleansing product, and said one or more dispensers configured to dispense skin conditioning product;
   each of said dispensers in communication with the dispenser usage compliance system; and configured to provide a signal to the dispenser usage monitoring system, the signal indicating usage of the dispenser including an indication of the time of usage of the dispenser,
   the dispenser usage monitoring system configured to compare the uses of said one or more dispensers configured to dispense skin protection product, said one or more dispensers configured to dispense skin cleansing product, and said one or more dispensers configured to dispense skin conditioning product to a skin care regime that specifies use of a plurality of hand products, each hand product providing one or more of skin protection, cleansing, and conditioning, and the skin care regime specifying circumstances under which each hand product should be used, the circumstances including prior to work activities, after identified activities that require use of one or more hand products, and completion of a work period, and
   the dispenser usage monitoring system is further configured to evaluate compliance with the skin care regime by comparing the times of uses of said one or more dispensers configured to dispense skin protection product, said one or more dispensers configured to dispense skin cleansing product, and said one or more dispensers configured to dispense skin conditioning product to the timings of uses of hand products identified by the skin care regime.

2. The system of claim 1, wherein determination of the level of compliance includes determining a ratio between a numerator indicative of the number of skin conditioning product uses, as determined by the monitoring system and a denominator indicative of the total number of skin conditioning product applications consistent with the skin care regime.

3. The system of claim 1, wherein
   the skin protection product is a pre-work hand product;
   the skin cleansing product is a washing product;
   the skin conditioning product is a post-work product; and
   the skin care regime comprises:
   applying the pre-work hand product at the start of a working shift in the work place;
   during the working shift washing hands using a washing product; and
   after use of a washing product, applying the conditioning product as determined by the skin care regime based on intervening time to return to work; and
   after use of a washing product, applying the post-work product as determined by the skin care regime based on intervening time to return to work.

4. The system of claim 1, wherein determination of the level of compliance includes determining a ratio between a numerator indicative of the number of skin protection product uses, as determined by the monitoring system and a denominator indicative of the total number of skin protection product applications consistent with the skin care regime.

* * * * *